United States Patent [19]
Noishiki

[11] Patent Number: 5,986,168
[45] Date of Patent: Nov. 16, 1999

[54] PROSTHESIS CONTAINING BIOABSORBABLE MATERIALS INSOLUBILIZED WITHOUT CHEMICAL REAGENTS AND METHOD OF MAKING THE SAME

[75] Inventor: Yasuharu Noishiki, Yokohama, Japan

[73] Assignee: Nicem, Ltd., Yokohama, Japan

[21] Appl. No.: 08/928,752

[22] Filed: Sep. 12, 1997

Related U.S. Application Data

[63] Continuation of application No. 08/571,557, Dec. 13, 1995, abandoned.

[30] Foreign Application Priority Data

Apr. 25, 1995 [JP] Japan .................................. 7-100995

[51] Int. Cl.$^6$ ....................................................... A61F 2/02
[52] U.S. Cl. ................................................................. 623/11
[58] Field of Search .................................. 623/1, 11, 12, 623/66, 901; 424/422, 423

[56] References Cited

U.S. PATENT DOCUMENTS

| | | |
|---|---|---|
| 3,376,869 | 4/1968 | Borysko . |
| 3,425,418 | 2/1969 | Chvapil et al. . |
| 3,742,955 | 7/1973 | Battista et al. . |
| 3,810,473 | 5/1974 | Cruz, Jr. et al. . |
| 4,016,877 | 4/1977 | Cruz, Jr. et al. . |
| 4,066,083 | 1/1978 | Ries . |
| 4,115,928 | 9/1978 | Riechenbacher . |
| 4,208,745 | 6/1980 | Okita . |
| 4,229,838 | 10/1980 | Mano . |
| 4,233,360 | 11/1980 | Luck et al. . |
| 4,238,480 | 12/1980 | Sawyer . |
| 4,271,070 | 6/1981 | Miyata et al. . |
| 4,286,341 | 9/1981 | Greer et al. . |
| 4,424,208 | 1/1984 | Wallace et al. . |
| 4,592,864 | 6/1986 | Miyata et al. . |
| 4,606,910 | 8/1986 | Sawyer . |
| 4,690,973 | 9/1987 | Noishiki et al. . |
| 4,695,281 | 9/1987 | Miyata et al. ............................... 623/1 |
| 4,704,131 | 11/1987 | Noishiki et al. . |
| 4,749,689 | 6/1988 | Miyata et al. . |
| 4,798,606 | 1/1989 | Pinchuk . |
| 4,801,539 | 1/1989 | Akasaka et al. . |
| 4,803,075 | 2/1989 | Wallace et al. . |
| 4,806,595 | 2/1989 | Noishiki et al. . |
| 4,833,200 | 5/1989 | Noishiki et al. . |
| 4,837,285 | 6/1989 | Berg et al. . |
| 4,970,298 | 11/1990 | Silver et al. . |
| 5,035,708 | 7/1991 | Alchas et al. . |
| 5,043,426 | 8/1991 | Goldstein . |
| 5,080,670 | 1/1992 | Imamura et al. . |
| 5,131,907 | 7/1992 | Williams et al. . |
| 5,137,875 | 8/1992 | Tsunenaga et al. . |
| 5,171,261 | 12/1992 | Noishiki et al. . |
| 5,230,693 | 7/1993 | Williams et al. . |
| 5,256,418 | 10/1993 | Kemp et al. ............................. 424/423 |
| 5,263,984 | 11/1993 | Li et al. . |
| 5,314,874 | 5/1994 | Miyata et al. . |
| 5,376,376 | 12/1994 | Li . |
| 5,387,236 | 2/1995 | Noishiki et al. . |

FOREIGN PATENT DOCUMENTS

| | | |
|---|---|---|
| 0089145 | 3/1982 | European Pat. Off. . |
| 0132979 | 7/1983 | European Pat. Off. . |
| 0196197 | 3/1985 | European Pat. Off. . |
| 0212881 | 7/1985 | European Pat. Off. . |
| 0268421 | 11/1986 | European Pat. Off. . |
| 0411124 | 3/1988 | European Pat. Off. . |
| 531547 | 3/1993 | European Pat. Off. . |
| 1491218 | 4/1969 | Germany . |
| 62-26230 | of 1987 | Japan . |
| 904693 | 2/1988 | U.S.S.R. . |
| 1213054 | 11/1970 | United Kingdom . |

OTHER PUBLICATIONS

Jinko Zoki (Artificial Organs) vol. 19, No. 3, (1990), 1235–1238 (abstract only).

*Primary Examiner*—David J. Isabella
*Assistant Examiner*—Choon P. Koh
*Attorney, Agent, or Firm*—Varndell & Varndell, PLLC

[57] ABSTRACT

The present invention relates to a prosthesis comprising one or more bioabsorbable substances insolubilized and/or immobilized in place by a physical method which excludes chemical reagents. A growth factor can be bound to the bioabsorbable substance for simulating growth of, for example, fibroblast and endothelial cells, around and into the prosthesis. The invention can include a porous fabric substrate having the bioabsorbable substance(s) insolubilized and immobilized therewithin by one or more of the physical methods. The physical method can include entanglement, dry-up, thermal crosslinkng, gamma irradiation, ultraviolet irradiation, or swelling up by hyper hydration with electric charge. The invention excludes the use of conventional chemical reagents, such as glutaraldehyde or formaldehyde, which are toxic. Since the invention does not use the chemical reagents of the prior art, it can avoid the toxicity and foreign body reaction problems associated therewith. The prosthesis of the invention does not have blood leakage and provides an excellent antithrombogenicity by rapid completion of neointima formation with endothelial cell lining at an early stage after implantation.

28 Claims, No Drawings

PROSTHESIS CONTAINING BIOABSORBABLE MATERIALS INSOLUBILIZED WITHOUT CHEMICAL REAGENTS AND METHOD OF MAKING THE SAME

This application is a continuation application of Ser. No. 08/571,557, filed Dec. 13, 1995 now abandoned.

BACKGROUND OF THE INVENTION

This invention relates to a prosthesis for implantation into a mammal comprising bioabsorbable substances insolubilized by physical methods, instead of chemical-reagent cross-linking, that can be used in place of conventional prostheses coated with bioabsorbable substances and to cytokines insolubilized on the bioabable substances. The invention also relates to a method of manufacturing such prostheses.

1. Field of the Invention

This invention concerns a prosthesis comprising bioabsorbable substances that can prevent blood leakage, has non-thrombogenic property and host cell afnnity, and is free from side effects caused by chemical reagents typically used during the manufactuting process of conventional prostheses. The prosthesis can include growth factor, such as fibroblast growth factor, for stimulating growth of cells into and around the prostheses, such as fibroblasts and/or endothelial cells.

2. Description of the Prior Art

Important and necessary characteristics for a prosthesis are nondegradation strength in vivo, adequate mechanical properties such as morphology retention, softness and flexibility, nonblood leakage and the followings:

(1) Excellent nonthrombogenic effect, (2) Biological acceptability, such as nontoxicity, noncarcinogenicity, nonimmunogenicity and nonforeign body reaction, and (3) Excellent healing ability of neointima.

Most cardiovascular wall prostheses are made of woven, knitted or braided polyester fibers or expanded polytetrafluoroethylene. To obtain good neointima formation, a porous substrate has been adopted for the prostheses.

To prevent blood leakage through the porous prostheses, they are uually sealed with fresh blood before implantation. This procedure is called "preclotting." Recently, conventional cardiovascular wall prostheses are coated with bioabsorbable substances such as collagen, albumin or gelatin during their manufacturing process instead of predotting during surgery.

These bioabsorbable substances are insolubilized by cross-linking with a chemical reagent such as glutaraldehyde, formaldehyde or diisocyanate. They are, however, cytotoxic, and even after a long period of time, adverse side effects result in causing foreign body reaction against the host tissues. According to recent scientific papers, it is recognized that the healing is always delayed due to noninfectious inflammation, fluid retention around the prosthesis, and/or unusually continuous fever after implantation.

When conventional vascular prostheses are used, porous ones may be selected to yield tissue ingrowth from the adventitia side to the luminal side. Usually, these pores are sealed with a fibrin network produced by fresh blood (preclotting). However, the fibrin network produced by preclotting always has some risk of being dissolved because of fibrinolysis phenomenons. This is especially true when a large amount of anticoagulants is used during and after implantation, and bleeding due to fibrinolysis can result in serious patient conditions. To prevent such undesired bleeding, recent porous vascular prostheses are coated with bioabsorbable substances cross-linked with glutaraldehyde, formaldehyde or diisocyanate. In the present invention, alternative means or methods for such chemical cross-linking is used, as described below.

As to conventional coated prostheses, collagen, gelatin and albumin can be used as bioabsorbable substances. These bioabsorbable substances originally have high affinity to host cells unless they are chemically treated. They can induce an excellent neointima fonration without side effects before chemical treatment, however, their advantages are not employed satisfactorily. From the stand point of safety against bleeding during surgery, conventional coated prostheses have been used in humans despite of their adverse side effects, since recent surgeries require a large amount of anticoagulants during and after implantation. As a natural consequence, undesirable results after conventional prosthesis implantation have been reported in cases of old and/or weak patients, generally patients with poor or high risk conditions. When emphasis is placed on prevention of blood leakage, prevention of the side effects by the coated substances is difficult. This dilemma has been impossible to solve as long as the conventional coated prostheses have been used.

As for the manufacturing process, a highly viscous suspension of the bioabsorbable substances has been used in order to coat and impregnate the conventional prostheses. However, these substances only accumulate on the luminal surface due to their high viscosity, which tends to result in insufficient impregnation inside the prosthesis wall and easy detachment of impregnant from the surface of the prosthesis.

SUMMARY OF THE INVENION

This invention avoids the disadvantages of conventional prostheses. The invention can include the following:

1. A prosthesis comprising a porous substrate and one or more bioabsorbable substances that are insolubilized by at least one physical method such as entanglement, dry-up, thermal cross-linking, gamma irradiation, ultraviolet irradiation, and swelling up by hyper hydration with electric charge. These physical methods do not require chemical reagents which are used for conventional coated prostheses. The prosthesis of the invention can include growth factors, such as fibroblast growth factor, for increasing the rate of acceptance by the host of the implanted prothesis. The invented prosthesis can provide a high affinity for host cells and is free from the side effects caused by chemical reagents.

2. The prosthesis retaining one or more bioabsorbable substance by physical means rather than chemical means of this invention can be prepared by way of repeated inflitration of a porous prosthesis with a dispersed solution of a bioabsorbable substance having low viscosity, such as a viscosity at 22° C. of less than or equal to 1000 mpa's measured with viscometer. When collagen fiber is used as the bioabsorbable substance, the dispersed solution can be a fiber collagen suspension, where the concentration of the collagen is equal to or less than about 1.0 wt. %. Ihe prosthesis can be placed in the collagen fiber solution and/or the collagen fiber solution can be placed inside the prosthesis substrate, and the collagen fibers can be captured within the prosthesis substrate wall, such as within the pores of the prosthesis substrate wall, by providing a pressure differential between inside and outside of the prosthesis. The captured bioabsorbable substance(s) (i.e., collagen fibers) are insolubilized by a physical method, such as entanglement, dry-up, thermal cross-linking, gamma irradiation, ultraviolet irradiation and swelling up by hyper hydration with electric charge. Thereafter, growth factors, such as fibroblast growth factor, can be bound to the bioabsorbable substance(s).

3. A prosthesis made of bioabsorbable substance(s) where the bioabsorbable substance(s) is shaped by itself into a prosthesis without the need for the supporting structure of a porous substrate, and then immobilizing or insolubilizing the bioabsorbable materials in place by the physical method of this invention, such as by dry-up, thermal cross-linking, gamma irradiation, ultraviolet irradiation, and/or swelling up by hyper hydration with electric charge. After the immobilizing or insolubilizing of the bioabsorbable substance(s), growth factors, such as fibroblast growth factor, can be bound thereto.

DESCRIPTION OF THE PREFERRED EMBODIMENTS

In manufacturing the cardiovascular wall prosthesis relating to this invention, a conventional porous prosthesis such as porous fabric vascular prostheses or e-PTFE prostheses with long fibrils can be adopted as the framework to shape the prosthesis. The porous fabric is used to provide an appropriate structure to the prosthesis. Accordingly, porous tubes can be use when preparing a cardiovascular wall prosthesis. When another shape for the prosthesis is desired, porous fabrics in nontubular shapes can be used. For example, porous fabric in the form of a sheet can be used when preparing a wound dressing or a skin graft. It is also possible to eliminate the porous fabric substrate, especially when the shape of the prosthesis is simple. For example, when making a wound dressing or a slin graft, the bioabsorbable material itself can be shaped into the form of a sheet or a sponge-like material having a relatively small thickness compared to its length and width.

The prosthesis made with bioabsorbable materials or a porous substrate coated with bioabsorbable substances is physically treated for immobilizing the bioabsorbable materials in place and insolubilizing the bioabsorbably materials without the use of a chemical reagent such as glutaraldehyde, formaldehyde, or diisocyanate. Typically, glutaraldehyde, formaldehyde, or diisocyanate has been used in the past for insolubilizing the bioabsorbable substances of conventional coated prostheses. In the present invention the bioabsorbable substances are insolubilized and/or immobilized in place, such as attached to the porous substrate, by a physical method including entanglement, dry-up, thermal cross-linking, gamma irradiation, ultraviolet irradiation, or swelling up by hyper hydration with electric charge, instead of the conventional chemical reagent treatment. The physical immobilization or insolubilization methods of this invention is used in place of the chemical reagent treatments or reactions in the prior art and can be used for the immobilizing and/or insolubilizing either independently or in combination.

The expression "immobilizing or insolubilizing the bioabsorbable substance by physical methods" as used in this specification means any method of immobilizng and/or insolubilizing the bioabsorbable substance to itself or on the porous substrate that does not include the use of chemical reagents for insolubilizing, securing, immobilizing and/or cross-linking the bioabsorbable substances in place. The expression "insolubilizing and/or insolubilizing of the bioabsorbable substance in place" as used in this specification means that the prosthesis containing the bioabsorbable substance(s) can be rinsed under running water for about an hour with no detachment of the bioabsorbable substance(s) from the prosthesis. For example, as shown in a few of the examples of the invention set forth below, the prosthesis was rinsed in distilled runing water for 24 hours, and there was no sign of any detachment of the bioabsorbable substance(s) from the prosthesis surface. As explained above, the physical method of this invention can include entanglement, dry-up, thermal cross-linking, gamma irradiation, ultraviolet irradiation, and swelling up by hyper hydration with electric charge. Entanglement can include the use of a bioabsorbable substance in the form of a fiber, such as a collagen fiber or a collagen fiber coated with another bioabsorbable substance, where the fibers are so entangled with the porous substrate or themselves that they are not detached from the prosthesis when rinsed under running water. Dry-up or thermal cross-linking includes drying the prosthesis containing bioabsorbable substance(s) either at room or elevated temperature, so that the bioabsorbable substances are not detached from the thus dried prosthesis when it is subsequently rinsed under running water. Swelling up with hyper hydration with electric charge includes providing the bioabsorbable substance with a negative electric charge, so that when wetted the electrically charged substances inside the framework of the bioabsorbable substance alone or together with the substrate can swell up with water absorption by repulsion of electric charge with each other. This swelling action assists in holding the bioabsorbable substance(s) in place or within the substrate. With the hyper hydration, the bioabsorbable substances can become insoluble and thus cannot come out from the framework of the prosthesis. In order to provide a negative charge to bioabsorbable substances (such as collagen, gelatin, fibroin cellulose and chitin), succinylation and sulfonation are useful, together with any other method that can impart the negative charge to the bioabsorbable substances.

An objective of the invention is to provide a prosthesis comprising a porous substrate and bioabsorbable substance(s) immobilized thereon, which is free from the influence of chemical reagents. The inventive prosthesis has a high affinity for host cells, no blood leakage, a nonthrombogenic property, a noncarcinogenic property, and a good neointima formation, and is soft and pliable, without foreign body reaction.

Another objective of this invention is to provide a method of manufacturing a prosthesis that is free from the side effects caused by chemical reagents, while still having a high host cell affinity, no blood leakage property, a non-thrombogenic property, a soft and pliable property, a non-carcinogenic property and a good neointima formation without foreign body reaction.

A further objective of this invention is to provide a prosthesis containing bioabsorbable substance(s) that is negatively charged, which have a cytokine bound thereto, or a tissues or cells capable of generating a cytoldne. The cytokies can provide growth factors for promoting fibroblast and capillary blood vessel growth into and around the prosthesis.

In order to achieve the above objectives, a framework suitable for manufacturing the prosthesis can be as follows. The prosthesis is shaped from a porous substrate whose pores promote rapid tissue ingrowth from the adventitia side to the luminal side after implantation. In this invention, the porous substrate is not limited and can be in the form of a tube or a sheet of appropriate size. Further, the material of the porous substrate is not limited and can be polyester (such as Dacron® made by Du Pont de Nemours & Co.), polyurethane, polyvinyl alcohol, polyvinyl copolymer, nylon, polypropylene, polytetrafluoroethylene, cotton, and silk. Preferable substrates include conventional porous polyester prostheses, such as porous fabric vascular prostheses and e-PTFE prostheses with long fibrils.

The growth factors can be bound directly to the bioabsorbable substance(s). Bioabsorbable substances such as heparin, heparan sulfate, chondroitin sulfate, dennatan sulfate, hyaluronic acid, and succinylated collagen have a good affinity for binding or immobilizing the growth factor (s) within the prosthesis, so that the growth factor(s) can be gradually released in vivo after the prosthesis is implanted into a host. Alternatively, tissues or cells which release or secrete a growth factor can be bound or immobilized on the bioabsorbable substance(s). In some case, the bioabsorbable substances in the form of tissues or cells can be used for the tissues or cells which release or secrete a growth factor. For example, bone marrow tissues and cells, which can produce or secrete bFGF, can be used for the bioabsorbable substance. Physical treatment of such tissues and cells for insolubjiing or immobilizng them within the prosthesis by entanglement or other methods, which do no kill or diminish the kiling of the cells or tissues, is preferred, because this permits the tissues and cells to release growth factor(s) over a longer period of time in vivo after the prosthesis is implanted into a host. The release or secretion of the growth factor from the prosthesis can be effective for stimulating the growth of desired cells, such as fibroblasts, smooth muscle cells, and endothelial cells, at very low concentrations. For example, effective concentrations of growth factor(s) around the prosthesis of the invention for promoting cell growth can be as low as $1 \times 10^{-9}$ to $1 \times 10^{-11}$ M. This is because their action is mediated by their association with specific, high affinity receptors (growth factor receptors) expressed by the target cell. In the invention the target cells for the growth factor are those of the host surrounding the prosthesis after implantation.

It is also possible to omit the porous substrate by forming the bioabsorbable substance(s) itself into a prosthesis. For example, a solution or slurry containing, for example, about 1 to about 2 wt. % collagen or gelatin solution can be freezedried and molded into a piece of sponge. Heparin or other substances can be included in the solution or slurry that have an ainity for binding to cytokines, so that after the sponge is formed, it is dipped in a solution of the cytokine for providing growth factors to the prosthesis. The resulting sponge having growth factors contained can be used as is, or it can be crushed in a solution to provide a collagen sponge suspension, and the suspension injected into a mammal where the growth factors are desired. By controlling the pH of the collagen solution, collagen in the form of a powder can be formed. See, for example, the procedures of U.S. Pat. No. 4,749,689, which is incorporated herein by reference. If heparin or other substance having an affinity for binding cytolines thereto is contained in the collagen solution used to prepare the collagen powder, the powder can be contacted with a cytokine for binding the cytokine thereto. The resulting powder can be place on open wounds or injected into a mammal at a location where the growth factor of the cytokine is desired.

In this invention, any type of bioabsorbable substances, such as polyglycolic acid, polylactic acid-polyglycolic acid copolymer, bioabsorbable (3-hydroxybutylate-4-hydroxybutylate) polyester copolymer, polydioxane, collagen, gelatin, succinylated collagen, chrondroitin sulfate, succinylated gelatin, chitin, cellulose, fibroin, alginic acid, heparin, heparan sulfate, hyaluronic acid, dermatan sulfate and their derivatives can be used. The bioabsorbable substances are usually hydrophillic, although hydrophobic bioabsorbable substances are known and can be used in the present invention. The word "bioabsorbable substance" is used herein to define a material, preferably with low toxicity to its host, that is absorbed by the host over a period of time after implantation into the host. Among the aforelisted bioabsorbable materials, collagen, gelatin, succinylated collagen, succinylated gelatin, chitin, cellulose, fibroin, albumin, alginic acid, heparin, heparan sulfate, hyaluronic acid, chondroitin sulfate, dermatan sulfate and their derivatives are preferable. his substance can be monomolecular or polymolecular with a wide range of molecular weights depending on the particular material. For example, heparan sulfate and hyaluronic acid can be polymolecular materials respectively with a molecular weight from about 5,000 to about 20,000 and about 10,000 to about 2,000,000.

Since this invention does not use chemical treatments for the bioabsorbable substances for the insolubilization thereof or for the immobilizing or retaining of these substances on a prosthesis, there is no opportunity for these bioabsorbable substances to have their immunogenicity reduced by chemical reagents during the process of coating and insolubilization. Therefore, nonimmunogeric or less immunogenic substances such as gelatin, atelocollagen, and purified collagen fiber obtained from animal Achilles tendons are preferred. If the substances have strong immunogenlsity, they should be used after reducing their immunogenisity.

In addition to the above, tissues and cells of manmals can also be used for the bioabsorbable substances, especially autologous tissue and cells, namely, tissues and cells from the host into which the prosthesis is implanted. The advantages of using tissues and cells for the bioabsorbable substances include the following:

(1) The tissues and cells are large enough to be easily interstices of the porous substrates, as well as with each other.

(2) The tissues and cells can give suitable environment for host cell migration and proliferation even if they die during sterilization or drying up. If the tissues can maintain their living ability, they will act as promoters of neointima formation on the prosthesis surface.

(3) Autologous tissues and cells can synthesize some cytokines such as cell growth factors. With these cytokines, tissues and cells can maintain their living ability and stimulate each other to survive and to create organs where they are located.

The term "cytoline" as used herein is a term well known in the art as a collective term for the proteins that initiate or regulate cell to cell communication, for example, regulate cellular growth and differentiation, and are involved in healing, repair and the response to disease (e.g., inflammation, immunity and cancer cachexia). The activities of cytokines are broad and overlapping. Several cytokines have specific nomenclatures. These include tumor necrosis factor-alpha (TNF alpha, cachectin), TNF-beta (lymphotoxin), interferon-alpha, -beta and -gamma. Growth factors can also be cytokines. Growth factors can be defined as multifunctional, locally acting, intercellular signalling polypeptides which control both the ontogeny and maintenance of tissue form and function. Growth factors that can be used in the invention include: epidermal growth factor (EGF), platelet derived growth factor (PDGF), transforming growth factor-alpha and -beta (TGF), fibroblast growth factor (FGF, basic FGF, acidic FGF) and colony stimulating factor (CSF). New factors are continually added to the known cytokines, and new functions are continually reported for the known cytokines.

Especially useful growth factor cytokines for use in the present invention are fibroblasts growth factors, which can be obtained from natural cells (such as bFGF synthesized from bone marrow) by internal biotechnology. These are also commercially available and produced by biotechnology companies for commercial sale.

Preferred growth factors are basic fibroblasts growth factor (bFGF), vascular endothelial growth factor (VEGF), platelet-derived endothelial cell growth factor (PDGF), and Hepatocyte growth factor (HGF). BFGF is a powerful mitogen for a wide variety of cell types including, fibroblast, neurectodermal cells and capillary and large vessel endothelial cells. VEGF is a mitogen for endothelial cells. PDGF induces multiplication of fibroblasts and smooth muscle cells. BFGF and VEGF are especially preferred. These and other growth factors are commercially available from Genzyme Corporation, Cytokine Research Products, Boston, Mass., U.S.A. and other companies.

The bioabsorbable substance(s) can be encaptured easily by entanglement with porous structure of the prosthesis substrate. For this purpose, bioabsorbable substances with a filamentous shape or a large size (i.e., cells and tissues) are preferable, but those with a nonfilamentous shape or small size can also be used. To encapture the filamentous substances, a diluted suspension of the substance or its solution can be used having a viscosity at 22° C. of less than or equal to about 1000 mPa's as measured on a viscosity meter for a collagen fiber suspension, the concentration of the collagen can be equal to or less than about 1.0 wt. %. By using such a low viscous suspension, it is possible to enmesh the filamentous substances inside the prosthesis substrate by providing a pressure differential to the suspension between the inside and outside of the prosthesis substrate wall. The filamentous substances can be gradually accumulated inside the prosthesis wall as well as on the prosthesis substrate wall by enmeshing of this low viscous suspension and by passing it through pores of the prosthesis wall. If the suspension is highly viscous, filamentous substance(s) cannot penetrate the prosthesis since one filament obstructs the passage way though the interstices of the porous prosthesis substrate wall of another filament. With this procedure, a sufficient number of filaments are entangled with the porous framework of the prosthesis substrate.

After the foregoing procedures of impregnating the porous substrate with the bioabsorbable substance(s), such procedures can be repeated to provide an additional impregnation of a bioabsorbable substance on the cardiovascular prosthesis. For example, after the first impregnation, the graft is dried up, and a suspension or solution of another kind of bioabsorbable substance(s) is impregnated again into the pores of the prosthesis substrate, in which the former bioabsorbable substance has been present. Thereafter, the graft is dried up again, such as by freeze drying or drying in air.

The second or additional impregnation can make the prosthesis more useful if it is desirable to provide a cardiovascular wall prosthesis. For example, collagen fibers can be firstly impregnated onto or into the porous substrate and then heparin can be secondly impregnated onto or into the porous substrate. After these two impregnations, the prosthesis can obtain an antithrombogenic property as well as powerful negative charge inside the prosthesis wall, which is effective to retain a large amount of water inside the prosthesis. If collagen fibers are used as the first impregnant and dermatan sulfate as the second impregnant, the prosthesis can obtain high host cell affinity, since dermatan sulfate can provide an excellent environment for host cell migration. If alginic acid, heparan sulfate or hyaluronic acid is used as the second impregnant, the prosthesis can obtain characteristic properties respectively corresponding thereto.

Thermal cross-linking is a most suitable physical method for insolubilizing encaptured bioabsorbable substances. After complete drying, the prosthesis with bioabsorbable substance is heated in the range of temperature of about 100° C. to about 180° C. and for about 1 hour to about 48 hours. The heating parameters depend on the type of bioabsorbable substance, however, in case of succinylated collagen fibers, heating between about 130° C. to about 140° C. for about 10 hours to about 24 hours is preferred. By these procedures, the bioabsorbable substances are cross-linked by dehydration when they are heated. For example, hydroxyl groups in the substances cross-link by covalent bonding.

Gamma irradiation and ultraviolet irradiation are another preferable physical method for insolubilizing the bioabsorbable substances. Between two, the former may be more powerful and useful, since with the gamma irradiation, insolubilization and sterilization can be performed more simultaneously. Representative gamma and ultraviolet irradiation conditions are gamma or ultraviolet radiation at about 0.1 Mrad to about 5 Mrad, preferably about 2 Mrad to about 3 Mrad, in either dry or wet conditions and in an atmosphere of room air or nitrogen gas. These conditions are dependent on the particular bioabsorbable substance. For example, in the succinylated collagen, irradiation at 2.5 Mrad with moisture is preferred.

The bioabsorbable substance(s) immobilized or insolubilized within the prosthesis can be charged either negatively or positively. The prosthesis is preferably negatively charged since the negatively charged surface can prevent adhesion of platelets which have a negative charge. In addition, under wet conditions, the electrically charged substances inside the framework of the substrate and the bioabsorbable substance can swell up with water absorption by repulsion of electric charge with each other. This swelling action assists in holding the bioabsorbable substance in the porous substrate. With such hyper hydration, the substances become insoluble and cannot come out from the framework of the prosthesis. In order to provide a negative charge to absorbable substances (such as collagen, gelatin, fibroin cellulose, and chitin), succinylation and sulfonation are useful. However, other methods can be used that can impart the negative charge to the bioabsorbable substances.

VEGF and bFGF can be bound with various negatively charged substances, especially to which at least one of the following bioabsorbable substances is trapped such as heparin, heparan sulfate, chondroitin sulfate, dermatan sulfate, hyaluronic acid, succinylated collagen, etc. When a vascular prosthesis is prepared with these substances, these cytokines can be immobilized for slow release of the VEGF and bFGF in vivo. This procedure is applicable not only for a vascular implant, but also any kinds of biomaterials, such as those for accelerating wound healing such as wound dressings (including those similar to skin equivalent products), basement templates for wound healing, and stuffing substances for accelerating would healing and adhesion.

As to the manufacturng method of the cardiovascular wall prosthesis in this invention, the following method can be adopted: A method of manufacturing a cardiovascular wall prosthesis retaining a bioabsorbable substance by means of repeated infiltration into a tubular porous prosthesis substrate with a dispersed solution of bioabsorbable substances with a viscosity at 22° C. of less than or equal to about 1000 mPa's, and by capture of the bioabsorbable substances within the prosthesis substrate by providing a pressure differential between the inside and outside of the prosthesis substrate. A typical collagen fiber suspension can have a collagen concentration of less than or equal to about 1.0 wt. %. The captured bioabsorbable substances are then insolubilized and/or immobilized in place by a physical method such as entanglement, dry-up, thermal cross-linking, garnma irradiation, ultraviolet irradiation, and swelling up by hyper hydration with electric charge. The coated tubular prosthesis can then be cut opened to provide a sheet-like prosthesis, if desired.

The prosthesis of this invention can be used as cardiac wall prostheses and vascular prostheses, but the substances and the methods to produce them are also applicable in other fields, such as in tissue repair substitutes, wound dressings, and hemostats.

EXAMPLES

Example 1

A porous fabric vascular prosthesis was impregnated with negatively charged collagen fibrils, having a length of less than 2 cm and a thickness of less that 10 microns. The procedure showed complete sealing as follows: Collagen fibers obtained from bovine Achilles tendon were succinylated using a succinic anhydride, and suspended in distilled water at pH 4.5 with hyd oric acid or acetic acid to produce a 0.2 wt. % collagen suspension. The viscosity of the prepared collagen suspension was 800 mPa's at 22° C. which was measured by a typical viscometer. A fabric vascular prosthesis (Dacron® polyester having water porosity: 4,000 m/cm$^2$/min. at 120 mmHg) was enveloped by a vinyl chloride bag and connected to a syringe containing the suspension therein. By use of a three-way stopcock and a connecting tube, a closed circulation system was produced. The collagen suspension was infiltrated through the fabric vascular prosthesis wall by pressurized injection by means of the syringe. The portion of the suspension that passed through the wall was injected again with the syringe. This infiltrating procedure was repeated several times and collagen fibers became entangled in the pores of the prosthesis. Then the prosthesis was dipped into a 0.1 N sodium carbonate solution to neutralize residual acid around the collagen fibers and washed from inside several times by distilled water to remove the free remnants of collagen fiber from the luminal surface. Thereafter, the prosthesis was rinsed in cold running water for 24 hours, after which it was freeze-dried. Then the prosthesis was heated at 130° C. for 24 hours to thermally cross-link the collagen fibers and sterilized the coated prosthesis simultaneously. By this procedure, a porous fabric prosthesis impregnated with negatively charged fiber collagen was prepared.

Example 2

Microscopical structure and water permeability of the prosthesis produced by the method of Example 1 were evaluated as follows. By means of light microscopical observation of a cross section of the prosthesis, collagen fibers were observed to be contained in the interstices of the fibers of the polyester substrate. Scanning electron microscopical observation revealed that fibers of the polyester substrate and the collagen fibers were entangled in complex or complicated manner. The distance between adjacent collagen fibers was approximately 2 microns and the thickness of each collagen fiber is about 0.8 microns on the average. The amount of collagen fiber in the prosthesis wall was measured. The result is approximately 4 mg of collagen per cm$^2$ of the prosthesis wall was trapped on the prosthesis wall. Under a wet condition, the collagen fibers were found to retain approximately 100 mg/cm$^2$ of water. Therefore, a very small amount of collagen fiber can retain a large amount of water inside the prosthesis wall. Water permeability measurement revealed that the prosthesis resulting from Example 1 had a low porosity with water porosity 0.1 ml/cm$^2$/min. at 120 mmHg. These results indicated that the graft was sealed with a very small amount of collagen fibers and large amounts of water.

Example 3

The stability of collagen fibers entangled in the prosthesis produced by using the method of Example 1 was evaluated as follows: The prosthesis was rinsed in distilled runing water for 24 hours. The result was that there was no sign of collagen detachment from the prosthesis surface despite the long period of rinsing.

Example 4

The blood leakage from the prosthesis produced using the method of Example 1 was evaluated as follows: The prosthesis was implanted in the thoracic descending aorta of a dog without preclotting. During surgery and up to one week after implantation, the prosthesis did not show blood leakage through the prosthesis wall. The prosthesis was proved to be safe against blood leakage.

Example 5

The prosthesis produced using the method of Example 1 was evaluated as a cardiac wall prosthesis as follows: The prosthesis was cut in the longitudinal direction to produce a membrane as cardiac wall prosthesis. This was implanted as a cardiac wall patch in the right ventricular-pulmonary artery outflow tract of a dog. The prosthesis was very soft and pliable. Therefore, it was easy to fit with the thick cardiac wall and the thin pulmonary arterial wall as well. After implantation, the dog was systemically heparirdzed (300 IU/kg), however, the prosthesis wall did not show any blood leakage. From this experiment, the prosthesis showed its safety against the hepariniztion of blood, and proved to be suitable prosthesis as a cardiac wall patch.

Example 6

The prostheses (10 mm in internal diameter and 6 cm in length) produced using the method of Example 1 was implanted in the descending thoracic aortae of three dogs without preclotting. The prostheses turned red in color just after implantation, however, there was no blood leakage through the prosthesis wall. On the first day after implantation, the prosthesis was retrieved from one of the three dogs. The luminal surface of the prosthesis was covered with thin layer of fibrin. By means of light microscopy, dense network of collagen fibers was noticed in the interstices of the fibers of the polyester substrate. Numerous erythrocytes, leukocytes platelets and fibrin fibers were trapped inside the collage network The luminal surface was free from thrombus deposition. On the 10th day after implantation, the second prosthesis was removed from another dog. The luminal surface of the prosthesis was non-glistening white in color. By means of light microscopy, the luminal surface was covered with thin layer of fibrin. In the middle layer of the prosthesis was composed of polyester fibers of the substrate, collagen fibers, and fibrin network. Some fibroblasts were observed in the interstices of the collagen fibers. Around the outside of the prosthesis there were numerous fibroblasts, and capillary blood vessels, but no giant cells, plasma cells or lymphocytes, suggesting no foreign body reaction around the prosthesis. The prosthesis showed high affinity to the host cells. Six months after implantation, the third prosthesis was removed. The luminal surface was glistening white without thrombus deposition. By means of light microscopy, the luminal surface was completely lined by a continuous and single layer of endothelial cells. Multiple layers of smooth muscle cells were noticed underneath the endothelial cells. Inside the prosthesis wall, numerous fibroblasts and capillary blood vessels migrated, but there were no collagen fibers, which had been observed since just after implantation. The collagen fibers were already absorbed. In the adventitia side, the graft surface was completely covered with a connective tissue layer which contained numerous fibroblasts and capillary blood vessels. There was no foreign body reaction around and inside the prosthesis wall. From these observations, the invented prosthesis was proved to be safety graft with good property for neointima formation and no foreign body reactions.

Example 7

Using the method of Example 1, a prosthesis sealed with collagen was obtained. It was cut in the longitudinal direction as shown in the Example 4 to obtain a cardiac wall prosthesis. Three cardiac wall prostheses were implanted in the outflow tract of dogs according to the procedure of Example 5. They were removed on 1 and 10 days and 6 months after surgery, respectively. Results similar to Example 6 were obtained macroscopically and microscopically.

Example 8

A long fibril ePTFE prosthesis substrate was coated with succinylated atelocollagen using a similar method of Example 1 with the exception that gamma irradiation was used instead of thermal cross-linking and any other differences as set forth below. The treatment showed complete sealing as follows: Succinylated atelocollagen suspension (0.2 wt. %) was sieved through the ePTFE prosthesis substrate of fibril length 90 micron by pressurized injection. Repeating this sieving procedure several times resulted in that the pores of the prosthesis became sealed with atelocollagen. The prosthesis was dried in air, and then irradiated with gamma irradiation of 2.5 Mrad under moisture condition, where the prosthesis was simultaneously sterilized. By means of light microscopical observation of a cross section of the prosthesis, collagen fibers were observed in the interstices of ePTFE. By means of scanning electron microscopy, collagen fibers were observed as enmeshed into the interstices of fibrils of ePTFE in a complex or complicated manner. The distance between adjacent collagen fibers was approximately 2 microns on the average. The water permeability of the prosthesis was 0.1 ml/cm$^2$/min. at 120 mmHg.

Example 9

The stability of the atelocollagen on the prosthesis produced using the method of Example 8 was evaluated as follows: The prosthesis was rinsed in distilled running water for 24 hours. The result was that there was no sign of collagen detachment from the prosthesis surface.

Example 10

The blood leakage from the prosthesis produced using the method of Example 8 was evaluated as follows: The prosthesis was implanted in place of the abdominal aorta of a dog without the preclotting of the prior art. During surgery and up to one week after implantation, the prosthesis did not show blood leakage through the prosthesis wall. The prosthesis was proved to be safe against the blood leakage.

Example 11

The prosthesis produced using the method of Example 8 was evaluated as a cardiac wall prosthesis as follows: The prosthesis was cut in the longitudinal direction to produce a membrane as cardiac wall prosthesis. This was implanted as a cardiac wall patch in the right ventricular-pulmonary artery outflow tract of a dog. The prosthesis was very soft and pliable. Therefore, it was easy to fit with the thick cardiac wall and the thin pulmonary arterial wall as well. After implantation, the animal was systemically heparinized (300 IU/kg), however, the prosthesis wall did not show any blood leakage. From this experiment, the prosthesis showed its safety against the heparinization of blood, and proved to be suitable prosthesis as a cardiac wall patch.

Example 12

Prostheses (6 mm in internal diameter and 6 cm in length) produced using the method of Example 8 were respectively implanted in the abdonal aortae of ftree dogs without preclottng. The prostheses turned red in color just after implantation, however, there was no blood leakage through the prosthesis wall. On the first day after implantation, the prosthesis was retrieved from one of the three dogs. The luminal surface of the prosthesis was covered with thin layer of fibrin. By means of light microscopy, dense network of collagen fibers was noticed in the interstices of ePTFE filaments. Numerous erythrocytes, leukocytes platelets and fibrin fibers were trapped inside the collage network. The luminal surface were free from thrombus deposition. Another two grafts were retrieved at 10 days and 6 months after implantation, respectively. Results similar to Example 5 were obtained macroscopically and microscopically.

Example 13

Using the method of Example 8, a prosthesis sealed with collagen was obtained. It was cut in the longitudinal direction as shown in the Example 5 to obtain a cardiac wall prosthesis. Three cardiac wall prostheses were respectively implanted in the outflow tract of dogs according to the procedure of Example 5. They were removed on 1 and 10 days and 6 months after surgery, respectively. Results similar to Example 5 were obtained macroscopically and microscopically.

Example 14

A long fibril ePTFE prosthesis substrate was coated with succinylated atelocollagen using a similar method of Example 1 with the exception that ultraviolet irradiation was used instead of thermal cross-linking and any other differences as set forth below. The treatment showed complete sealing as follows: Succinylated atelocollagen suspension (0.2 wt. %) was sieved through the ePTFE prosthesis substrate of fibril length 90 micron by pressurized injection. Repeating this sieving procedure several times resulted in that the pores of the prosthesis became sealed with atelocollagen. The prosthesis was dried in air, and then irradiated with ultraviolet irradiation of 2.5 Mrad under moisture condition, where the prosthesis was simultaneously sterilized. By means of light microscopical observation of a cross section of the prosthesis, collagen fibers were observed in the interstices of ePTFE. By means of scanning electron microscopy, collagen fibers were observed as enmeshed into the interstices of fibrils of ePTFE in a complex or complicated manner. The distance between adjacent collagen fibers was approximately 2 microns on the average. The water permeability of the prosthesis was 0.1 ml/cm$^2$/min. at 120 mmHg.

Example 15

The stability of the atelocollagen on the prosthesis produced using the method of Example 14 was evaluated as follows: The prosthesis was rinsed in distilled running water for 24 hours. The result was that there was no sign of collagen detachment from the prosthesis surface.

Example 16

The blood leakage from the prosthesis produced using the method of Example 14 was evaluated as follows: The prosthesis was implanted in place of the abdominal aorta of a dog without the preclotting of the prior art. During surgery and up to one week after implantation, the prosthesis did not show blood leakage trough the prosthesis wall. The prosthesis was proved to be safe against the blood leakage.

Example 17

The prosthesis produced using the method of Example 14 was evaluated as a cardiac wall prosthesis as follows: The prosthesis was cut in the longitudinal direction to produce a membrane as cardiac wall prosthesis. This was implanted as a cardiac wall patch in the right ventricular-pulmonary artery outflow tract of a dog. The prosthesis was very soft and pliable. Therefore, it was easy to fit with the thick cardiac wall and the thin pulmonary arterial wall as well. After implantation, the animal was systemically heparinized (300 IU/kg), however, the prosthesis wall did not show any blood leakage. From this experiment, the prosthesis showed its safety against the heparinization of blood, and proved to be suitable prosthesis as a cardiac wall patch.

Example 18

Prostheses (6 mm in internal diameter and 6 cm in length) produced using the method of Example 14 were respectively implanted in the abdominal aortae of three dogs without preclotting. The prostheses turned red in color just after implantation, however, there was no blood leakage through the prosthesis wall. On the first day after implantation, the prosthesis was retrieved from one of the three dogs. The luminal surface of the prosthesis was covered with thin layer of fibrin. By means of light microscopy, dense network of collagen fibers was noticed in the interstices of ePTFE filaments. Numerous erythrocytes, leukocytes platelets and fibrin fibers were trapped inside the collage network. The luminal surface were free from thrombus deposition. Another two grafts were retrieved at 10 days and 6 months after implantation, respectively. Results similar to Example 5 were obtained macroscopically and microscopically.

Example 19

Using the method of Example 14, a prosthesis sealed with collagen was obtained. It was cut in the longitudinal direction as shown in the Example 5 to obtain a cardiac wall prosthesis. Three cardiac wall prostheses were respectively implanted in the outflow tract of dogs according to the procedure of Example 5. They were removed on 1 and 10 days and 6 months after surgery, respectively. Results similar to Example 5 were obtained macroscopically and microscopically.

Example 20

Gelatin and heparin were used as the bioabsorbable substances. A long fibril ePTFE graft was coated with gelatin using a similar method of Example 8. Gamma irradiation was again used for immobilizing. The treatment resulted in complete sealing as follows: Succinylated gelatin was suspended (10 wt. %) and was sieved through an ePTFE prosthesis having a fibril length of 90 microns by pressurized injection, similar to the procedure used in Example 1. Repeating this sieving procedure several times resulted in the pores of the prosthesis becoming sealed by succinylated gelatin. Then the prosthesis was freeze-dried. A one weight percent heparin solution was impregnated into the freeze-dried prosthesis wall, and it was dried again. Gamma iradiation of 2.5 Mrad at moisture condition was performed and the resulting prosthesis wall, whereby the prosthesis was simultaneously sterilized. Results similar to Example 8 were obtained macroscopically and microscopically. The water permeability of the resulting prosthesis was 0.1 ml/cm$^2$/min. at 120 mmHg.

Example 21

The stability of the gelatin on the prosthesis produced using the method of Example 20 was evaluated as follows: The prosthesis was rinsed in distilled running water for 24 hours. The result was that there was no sign of gelatin detachment form the prosthesis surface Example 22

The antithrombogenicity of the prosthesis with heparin produced using the method of Example 20 was evaluated as follows: The prosthesis was implanted in the abdominal aorta of a dog without preclotting. During and after implantation, the prosthesis did not show blood leakage through the prosthesis wall. One hour after implantation, the prosthesis was retrieved. The luminal surface of the prosthesis showed no thrombus deposition at all. The prosthesis was proved to have antithrombogenic property by the heparin immobilization.

Example 23

Succinylated collagen and dermatan sulfate were used as the bioabsorbable substances. A porous fabric vascular prosthesis substrate was coated with negatively charged collagen fibrils. A fabric vascular prosthesis (Dacron® polyester, water porosity: 4,000 ml/cm$^2$/min. at 120 mmHg) was used as the substrate. Collagen fibers obtained from bovine Achilles tendons were succinylated using succinic anhydride, and suspended into distilled water at pH 4.5 with hydrochloric acid or acetic acid to produce a 0.2 wt. % collagen suspension. The collagen suspension was sieved through the fabric vascular prosthesis wall by pressurized injection by means of the syringe. The portion of the suspension that passed through the wall was injected again with the synnge. This sieving procedure was repeated several times, so that the collagen fibers were entangled in the pores of the prosthesis. The prosthesis was then freeze-dried. The freeze-dried prosthesis was dipped into a 1 wt. % of dermatan sulfate solution to impregnate the dermatan sulfate into the interstices of the fibers of the polyester substrate and the collagen fibers. Then the prosthesis was dried in air. The resulting prosthesis was heated at 130° C. for 24 hours to thermally cross-link the collagen fibers and dermatan sulfate, and to simultaneously sterilized. By means of light microscopical observation of a cross section of the finally resulting prosthesis, collagen fibers were observed to be in the interstices of the fibers of the polyester substrate. Scanning electron microscopical observation revealed that polyester fibers of the substrate and collagen fibers were entangled in a complicated or complex manner. The prosthesis had a low porosity water porosity 0 ml/cm$^2$/min. at 120 mmHg.

Example 24

The stability of the collagen and dermatan sulfate on the prosthesis produced using the method of Example 23 was evaluated as follows: The prosthesis was rinsed in distilled running water for 24 hours. The result was that there was no sign of collagen or dermatan sulfate detachment from the prosthesis surface.

Example 25

Host cell affinity of the prosthesis with collagen and dermatan sulfate produced using the method of Example 24 was evaluated as follows: The prosthesis was implanted in the abdominal aorta of a dog without preclotting. During surgery and up to one week after implantation, the prosthesis did not show blood leakage through the prosthesis wall. Ten days after implantation, the prosthesis was retrieved. The luminal surface of the prosthesis was covered with thin fibrin layer. Near the anastomotic sites, an endothelial cell lining was observed. At the adventitia side numerous fibroblasts actively migrated into interstices of polyester fibers of the substrate. The prosthesis was proved to have excellent host cell affinity by dermatan sulfate immobilization.

Example 26

A porous fabric vascular prosthesis was impregnated with tissues and cells. The procedure showed complete sealing and active cell migration and proliferation in the prosthesis wall as follows: Bone marrow was obtained from the iliac bone of an experimental dog under general anesthesia. It was suspended in saline solution. The suspension was injected into the lumen of a porous polyester prosthesis substrate (water permeability ml/cm$^2$/min. at 120 mmHg) with pressure. The portion of the suspension that passed through the prosthesis wall was sucked up and injected again. After several repeated injections, the prosthesis substrate wall was completely occupied and sealed with bone marrow and blood cells which are contained in the bone marrow tissue. Then the prosthesis was implanted in the abdominal aortic position of the animal from which the bone marrow was obtained. During the surgery and up to one week after implantation of the prosthesis, no bleeding through the prosthesis wall was observed. At 3 weeks after implantation, the prosthesis wall was completely sealed with endothelial cells. Inside the graft wall, bone marrow cells survived and synthesized basic Fibroblasts Growth factors (bFGF), which is a cytokine acting as an accelerating factor of capillary blood vessel and fibroblast growth. The bFGF was confirmed using monoclonal antibody staining of the prosthesis wall immunohystochemically. Around the bone marrow cells, numerous capillary blood vessels and fibroblasts migration and proliferation were observed. Nicely healed neointha was maintained in the prosthesis wall up to 3 months observation period.

Example 27

This example is exemplary of the coated prosthesis of this invention including basic fibroblasts growth factor (bFGF). A porous fabric vascular prosthesis substrate (water permeability: 1,200 ml/cm$^2$/min. at 120 mmHg, produced by InterVascular Co. Ltd.) was impregnated with a mixture suspension of 1 wt. % of succinylated collagen and 0.02 wt. % heparin with pressure. It was freeze-dried and was heated at 130° C. for 20 hours to thermally cross-link the collagen fibers each other and to the heparin molecules. Then it was rinsed in distilled running water to wash off unbound heparin. It was freeze-dried again and sterilized by ethylene oxide gas. To immobilize bFGF onto the vascular prosthesis, it was dipped into a solution of bFGF before implantation. For the measurement of bFGF binding, the prosthesis was dipped into a 100 ml saline solution containing 1 $\mu$g of radioisotope labeled bFGF for 30 minutes. Then it was rinsed in 500 ml of pure saline solution for 30 minutes three times to wash off free unbound bFGF. The amount of bFGF in the prosthesis was measured by means of a gamma counter. The results showed that the prosthesis can bind bFGF 0.01 $\mu$g/cm$^2$.

Example 28

This example is exemplary of the coated prosthesis of this invention containing bFGF. A porous polyester fabric vascular prosthesis substrate (water permeability: 1,200 ml/cm$^2$/min. At 120 mmHg) was impregnated with a mixture suspension of 1 wt. % of succinylated collagen and 0.02 wt. % heparin with pressure. It was freeze-dried and was heated at 130° C. for 20 hours to thermally cross-link the collagen fibers each other and to the heparin molecules. Then it was rinsed in distilled running water to wash out extra unbound heparin. It was freeze-ried again and sterilized by ethylene oxide gas. In the operating room, it was dipped in a 100 ml of saline solution containing 1 $\mu$g of bFGF for 30 minutes, and was rinsed in 500 ml of saline solution for 30 minutes three times to wash off unbound bFGF. Then it was implanted in the abdominal aortic position as a vascular substitute. During the surgery and up to one week after surgery, there was no bleeding through the prosthesis wall. At 3 weeks, the graft wall was covered with neointima having complete endothelial cell lining. Inside the graft wall, numerous capillary blood vessels are present resulted in acceleration of neointima formation.

Example 29

This example is exemplary of the coated prosthesis of the invention in the form of a sponge-like material that can be used as a wound dressing. A porous sponge made of fiber collagen was obtained using the following procedure. A 1 wt. % collagen slurry containing 0.02 wt. % heparin was freeze-dried to produce a collagen sheet of 5 cm$^2$ and 0.5 cm in thickness. Thereafter, it was heated at 130° C. for 20 hours to thermally cross-link the collagen fibers each other and to the heparin molecules. Then it was rinsed in distilled running water to wash off unbound heparin. It was freeze-dried again and sterilized by ethylene oxide gas. As an animal experiment, a 7 cm$^2$ skin wound was created on the back of a rabbit. The prepared collagen sponge was dipped in a 100 ml of saline solution containing 1 $\mu$g of bFGF for 30 minutes, and was rinsed in 500 ml of saline solution for 30 minutes three times to wash off unbound bFGF. Then it was inserted into the subcutaneous layer just under the created skin wound. One week after insertion, numerous capillary blood vessels were observed inside the collagen sheet. Numerous fibroblasts are also present. With these capillary and fibroblasts migration, the healing of the skin wound was accelerated. A pink colored granulation tissue was created in the bottom of the wound.

A control wound prepared in the manner but without insertion of collagen sponge of bFGF did not showed granulation formation. The control wound showed signs of healing, however, this was limited to the edge of the wound.

Example 30

This example is exemplary of the coated prosthesis of this invention made in the form of a sponge-like material that can be used as a wound dressing. A porous sponge made of fiber collagen was obtained using the following procedure. A 1 wt % collagen slurry containing 0.02 wt. % heparin was freeze-dried to produce a collagen sheet of 5 $cm^2$ and 0.5 cm in thickness. It was freeze-dried and was heated at 130° C. for 20 hours to thermally cross-link the collagen fibers each other and to the heparin molecules. Then it was rinsed in distilled running water to wash off unbound heparin. It was freeze dried again and sterilized by ethylene oxide gas. As an aninal experiment, a 7 $cm^2$ skin wound was created on the back of a rabbit. The prepared collagen sponge was dipped in a 50 ml of saline solution containing bFGF for 30 minutes, and was rinsed in 500 ml of saline solution for 30 minutes three times to wash off unbound bFGF. Then, the sponge was crushed in a 50 ml of saline solution to create a collagen sponge suspension. Then the suspension was injected into the subcutaneous layer just under the created skin wound. One week after insertion, numerous capillary blood vessels were observed in the areas where the collagen suspension was injected. The collagen sponge was almost absorbed, however, small pieces of suspended collagen sponge still remained in the subcutaneous layer. Numerous fibroblasts are also present. With these capillary and fibroblasts migration, the healing of the skin wound was accelerated. A pink colored granulation tissue was created in the bottom of the wound.

A control wound was prepared in the same manner without injection of collagen sponge suspension of bFGF did not showed granulation formation. The wound showed signs of healing, however, this was limited to the edge of the wound.

What is claimed is:

1. A prosthesis artificially made in vitro and comprising a time dependent immobilized and insolubilized bioabsorbable substance shaped into a prosthetic shape for implantation into a mammal, and having physical means for immobilizing and insolubilizing of the bioabsorbable substance for a predetermined period of time after implantation, the bioabsorbable substance being free from covalent bonding by chemical crosslinking of the bioabsorbable substance to another substance.

2. The prosthesis of claim 1, wherein the bioabsorbable substance is in the form of solid particles contained in a dispersion prior to the immobilizing and insolubilizing, and the physical means includes structure resulting from drying up the bioabsorbable substance.

3. The prosthesis of claim 1, wherein the physical means includes at least one of:
entanglement of the bioabsorbable substance,
structure resulting from thermally cross-linking the bioabsorbable substance,
structure resulting from gamma irradiating the bioabsorbable substance,
structure resulting from ultraviolet irradiating the bioabsorbable substance, and
structure resulting from hydrously swelling the bioabsorbable substance by electric charge.

4. The prosthesis of claim 1, further comprising a growth factor bound to the bioabsorbable substance.

5. The prosthesis of claim 1, comprising more than one bioabsorbable substance.

6. The prosthesis of claim 1, wherein the bioabsorbable substance is a member selected from the group consisting of collagen, gelatin, succinylated collagen, chondroitin sulfate, succinylated gelatin, chitin, cellulose, fibroin, albumin, alginic acid, heparin, heparan sulfate, hyaluronic acid, dermatan sulfate, derivatives of aforesaid members, and cells and tissues of mammals.

7. The prosthesis of claim 1, wherein the physical means includes a hydrously swelled bioabsorbable substance, where the hydrously swelled bioabsorbable substance is obtained by providing the bioabsorbable substance with a positive or negative charge and contacting a resulting charged bioabsorbable substance with water.

8. The prosthesis of claim 1, wherein the physical means includes a thermally cross-linked bioabsorbable substance, wherein the thermally cross-linked bioabsorbable substance is obtained by heating the bioabsorbable substance at a temperature of about 100° C. to about 180° C. and for about 1 hour to about 48 hours.

9. The prosthesis of claim 1, wherein the physical means includes a gamma irradiated bioabsorbable substances, wherein the gamma irradiated bioabsorbable substance is obtained by irradiating the bioabsorbable substance with gamma irradiation within a range of about 0.1 Mrad to about 5 Mrad.

10. The prosthesis of claim 1, wherein the physical means includes an ultraviolet irradiated bioabsorbable substance, wherein the ultraviolet irradiated bioabsorbable substance is obtained by irradiating the bioabsorbable substance with ultraviolet irradiation within a range of about 0.1 Mrad to about 5 Mrad.

11. The prosthesis of claim 1, comprising a porous substrate and the physical means immobilizes and insolubilizes the bioabsorbable substance onto the porous substrate.

12. The prosthesis of claim 11, further comprising a growth factor bound to the bioabsorbable substance.

13. The prosthesis of claim 11, wherein the bioabsorbable substance has a filamentous shape with a length of less than about 2 cm and a width of about 10 microns, and the physical means includes the bioabsorbable substance entangled with the porous substrate.

14. The prosthesis of claim 11, wherein the bioabsorbable substance is a member selected from the group consisting of collagen, gelatin, succinylated collagen, chondroitin sulfate, succinylated gelatin, chitin, cellulose, fibroin, albumin, alginic acid, heparin, heparan sulfate, hyaluronic acid, dermatan sulfate, derivatives of aforesaid members, and cells and tissues of mammals.

15. The prosthesis of claim 11, wherein the porous substrate is polyester fabric porous tube, the bioabsorbable substance is succinylated collagen fiber, and the physical means includes structure resulting from entanglement of the succinylated collagen fiber with the porous substrate and thermally cross-linking succinylated collagen fiber entangled with the porous substrate by heating at a temperature of about 100° C. to about 180° C. for about 1 hour to about 48 hours.

16. The prosthesis of claim 11, wherein the porous substrate is polyester fabric porous tube, the bioabsorbable substance is succinylated collagen fiber, and the physical means includes structure resulting from entanglement of the succinylated collagen fiber with the porous substrate and gamma irradiating succinylated collagen fiber entangled with the porous substrate, where the gamma irradiating uses gamma irradiation of about 0.1 Mrad to about 5 Mrad.

17. The prosthesis of claim 11, wherein the porous substrate is an expanded polytetrafluoroethylene tube, the bioabsorbable substance is succinylated collagen fiber, and the physical means includes structure resulting from entanglement of the succinylated collagen fiber with the porous substrate and thermally cross-linking succinylated collagen fiber entangled with the porous substrate by heating at a temperature of about 100° C. to about 180° C. for about 1 hour to about 48 hours.

18. The prosthesis of claim 11, wherein the porous substrate is an expanded polytetrafluoroethylene tube, the bioabsorbable substance is succinylated collagen fiber, and the physical means includes structure resulting from entanglement of the succinylated collagen fiber with the porous substrate and gamma irradiating succinylated collagen fiber entangled with the porous substrate, where the gamma irradiating uses gamma irradiation of about 0.1 Mrad to about 5 Mrad.

19. The prosthesis of claim 11, wherein the artificial means includes structure resulting from swelling of a portion of the bioabsorbable substance obtained by hyper hydration which includes providing the bioabsorbable substance with a negative charge and contacting resulting negatively charged bioabsorbable substance with water.

20. The prosthesis of claim 11, wherein the porous substrate is an expanded polytetrafluoroethylene tube, the bioabsorbable substance is succinylated collagen fiber, and the physical means includes structure resulting from entanglement of the succinylated collagen fiber with the porous substrate and ultraviolet irradiating succinylated collagen fiber entangled with the porous substrate, where the ultraviolet irradiating uses ultraviolet irradiation of about 0.1 Mrad to about 5 Mrad.

21. The prothesis of claim 11, wherein the bioabsorbable substance is bioabsorbable material onto which the bioabsorbable substance is immobilized and insolubilized by the artificial means; and the bioabsorbable substance and the bioabsorbable material are selected from the group consisting of collagen, gelatin, succinylated collagen, chondroitin sulfate, succinylated gelatin, chitin, cellulose, fibroin, albumin, alginic acid, heparin, heparan sulfate, hyaluronic acid, dermatan sulfate, derivatives of aforesaid members, and cells and tissues of mammals.

22. A prosthesis comprising a time dependent immobilized and insolubilized bioabsorbable substance free of covalent bonding by chemical crosslinking between the bioabsorbable substance and another substance and including physical means for immobilizing and insolubilizing the bioabsorbable substance, the physical means including the bioabsorbable substance having an artificially modified structure that prohibits detachment of the bioabsorbable substance from the prosthesis for a predetermined period of time after implantation, the artificially modified structure including an in vitro structure where a portion of the bioabsorbable substance is entangled in a manner that immobilizes the bioabsorbable substance in place during use.

23. The prosthesis of claim 22, wherein the physical means additionally includes at least one of:

entanglement of the bioabsorbable substance, structure resulting from thermally cross-linking the bioabsorbable substance, structure resulting from gamma irradiating the bioabsorbable substance, structure resulting from ultraviolet irradiating the bioabsorbable substance, and structure resulting from hydrously swelling the bioabsorbable substance by electric charge.

24. The prosthesis of claim 22, wherein the bioabsorbable substance is selected from the group consisting of collagen, gelatin, succinylated collagen, chondroitin sulfate, succinylated gelatin, chitin, cellulose, fibroin, albumin, alginic acid, heparin, heparan sulfate, hyaluronic acid, dermatan sulfate, derivatives of aforesaid members, and cells and tissues of mammals.

25. The prosthesis of claim 11, further comprising a porous substrate, wherein the bioabsorbable substance is in the form of a fiber and the artificially modified structure is entanglement of the bioabsorbable substance with the substrate.

26. The prosthesis of claim 25, wherein the physical means additionally includes at least one of:

structure resulting from thermally cross-linking the bioabsorbable substance, structure resulting from gamma irradiating the bioabsorbable substance, structure resulting from ultraviolet irradiating the bioabsorbable substance, and structure resulting from hydrously swelling the bioabsorbable substance.

27. The prosthesis of claim 26, wherein the bioabsorbable substance is selected from the group consisting of collagen, gelatin, succinylated collagen, chondroitin sulfate, succinylated gelatin, chitin, cellulose, fibroin, albumin, alginic acid, heparin, heparan sulfate, hyaluronic acid, dermatan sulfate, derivatives of aforesaid members, and cells and tissues of mammals.

28. A completely artificial prosthesis comprising a porous nonbioabsorbable substance and a time dependent immobilized and insolubilized bioabsorbable substance enmeshed in interstices of the porous nonbioabsorbable substrate and held in the interstices of the porous nonbioabsorbable substrate by thermal crosslinking without covalent bonding by chemical crosslinking of the bioabsorbable substance to the nonbioabsorbable substance, so that the bioabsorbable substance will remain in the interstices of the porous nonbioabsorbable substrate for a predetermined period of time after implantation.

* * * * *